United States Patent
Aue

(10) Patent No.: US 8,100,907 B2
(45) Date of Patent: Jan. 24, 2012

(54) JAWED SURGICAL INSTRUMENT FITTED WITH AN ELECTRODE AND A CABLE

(75) Inventor: Thomas Aue, Wedel (DE)

(73) Assignee: Olympus Winter & Ibe GmbH, Hamburg (DE)

( * ) Notice: Subject to any disclaimer, the term of this patent is extended or adjusted under 35 U.S.C. 154(b) by 1126 days.

(21) Appl. No.: 11/923,054

(22) Filed: Oct. 24, 2007

(65) Prior Publication Data

US 2008/0275441 A1    Nov. 6, 2008

(30) Foreign Application Priority Data

Nov. 8, 2006   (DE) .......................... 10 2006 052 407

(51) Int. Cl.
*A61B 18/18*    (2006.01)
(52) U.S. Cl. .............................. 606/52; 606/41; 606/45
(58) Field of Classification Search .............. 606/51–52, 606/205–207
See application file for complete search history.

(56) References Cited

U.S. PATENT DOCUMENTS

| 2,113,246 | A | * | 4/1938 | Wappler ........................ 606/205 |
| 5,282,800 | A | * | 2/1994 | Foshee et al. ................... 606/52 |
| 5,336,238 | A | * | 8/1994 | Holmes et al. ................. 606/208 |
| 5,603,723 | A | * | 2/1997 | Aranyi et al. .................. 606/205 |
| 5,607,449 | A | | 3/1997 | Tontarra |
| 5,618,308 | A | * | 4/1997 | Holmes et al. ................. 606/205 |
| 6,994,716 | B2 | * | 2/2006 | Jinno et al. ..................... 606/170 |
| 7,025,775 | B2 | * | 4/2006 | Gadberry et al. ............. 606/205 |
| 7,261,726 | B2 | * | 8/2007 | Jinno et al. ..................... 606/170 |
| 7,632,270 | B2 | * | 12/2009 | Livneh ............................ 606/51 |
| 2003/0018331 | A1 | | 1/2003 | Dycus et al. |

FOREIGN PATENT DOCUMENTS

| DE | 94 18 094 | 2/1995 |
| DE | 298 23 913 | 1/2000 |
| DE | 100 64 623 | 10/2007 |
| WO | 01/15614 | 3/2001 |
| WO | 2005/004735 | 1/2005 |

* cited by examiner

*Primary Examiner* — Linda Dvorak
*Assistant Examiner* — Amanda Scott
(74) *Attorney, Agent, or Firm* — Rankin, Hill & Clark LLP

(57) ABSTRACT

A jawed surgical instrument fitted at the distal end of a jaw head which is affixed at the distal end of a longitudinally elongated stem and which supports two mutually oppositely displaceable jaw parts, the jaw head being connectable by means of an actuation bar to one of two drive elements of a manipulating unit that are mutually oppositely displaceable in the stem direction, the other of the drive elements being connected to the stem. The jaw head comprises at least one electrode designed for tissue surgery and is electrically connected by means of the actuation bar to a cable issuing from the bar, the actuation bar and the jaw head being detachably connected to the manipulating unit wherein the actuation bar and the jaw head are detachably connected transversely to the stem direction or in the proximal direction parallel to the stem to the manipulating unit.

10 Claims, 2 Drawing Sheets

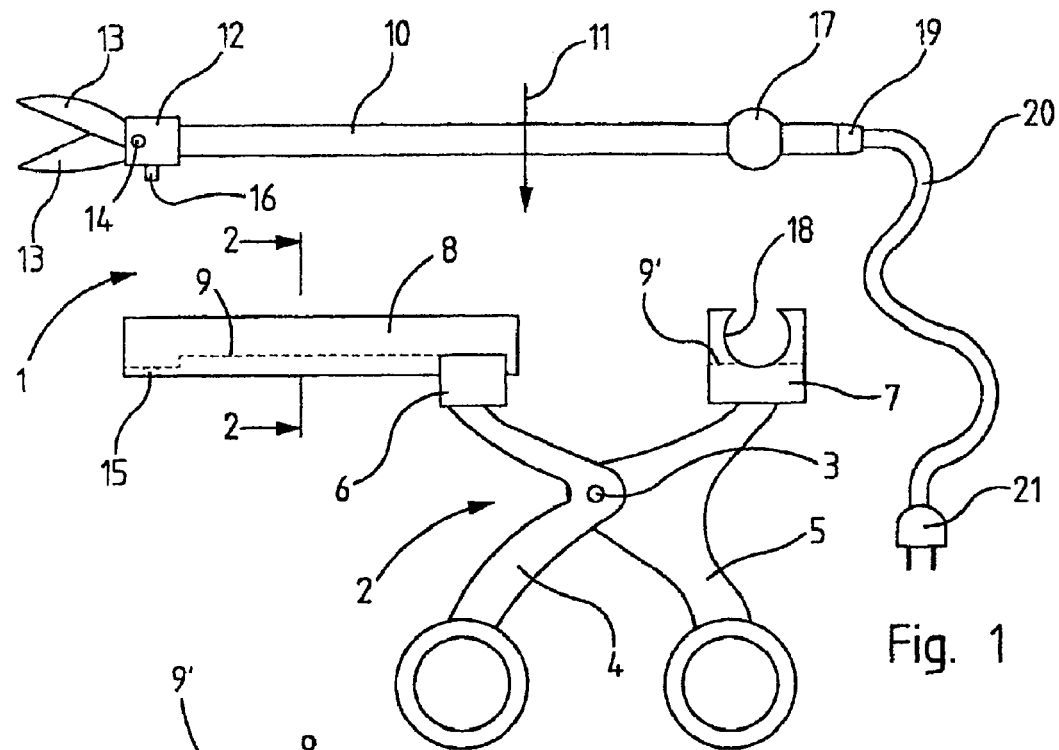
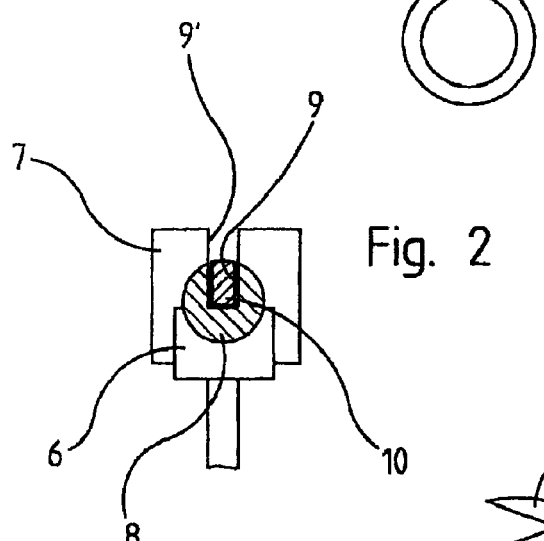
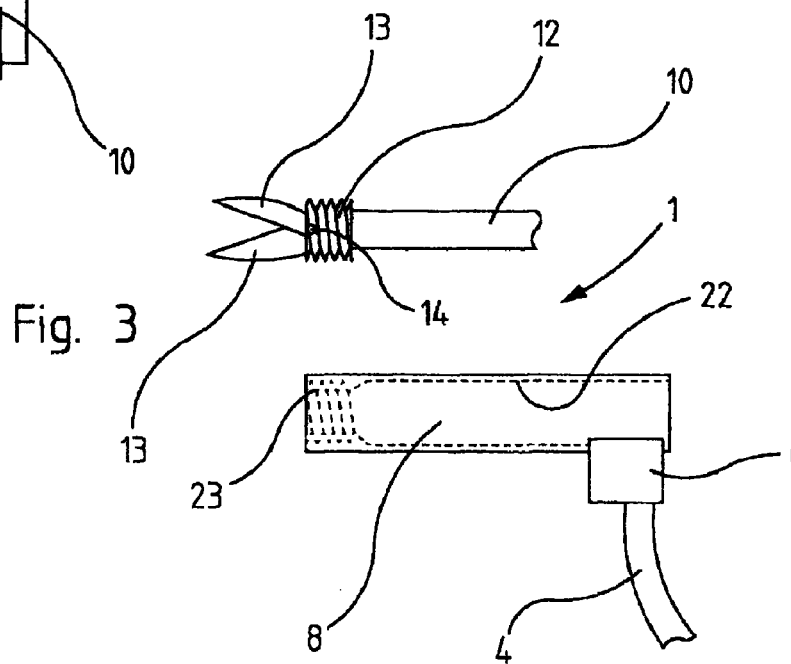
Fig. 1
Fig. 2
Fig. 3

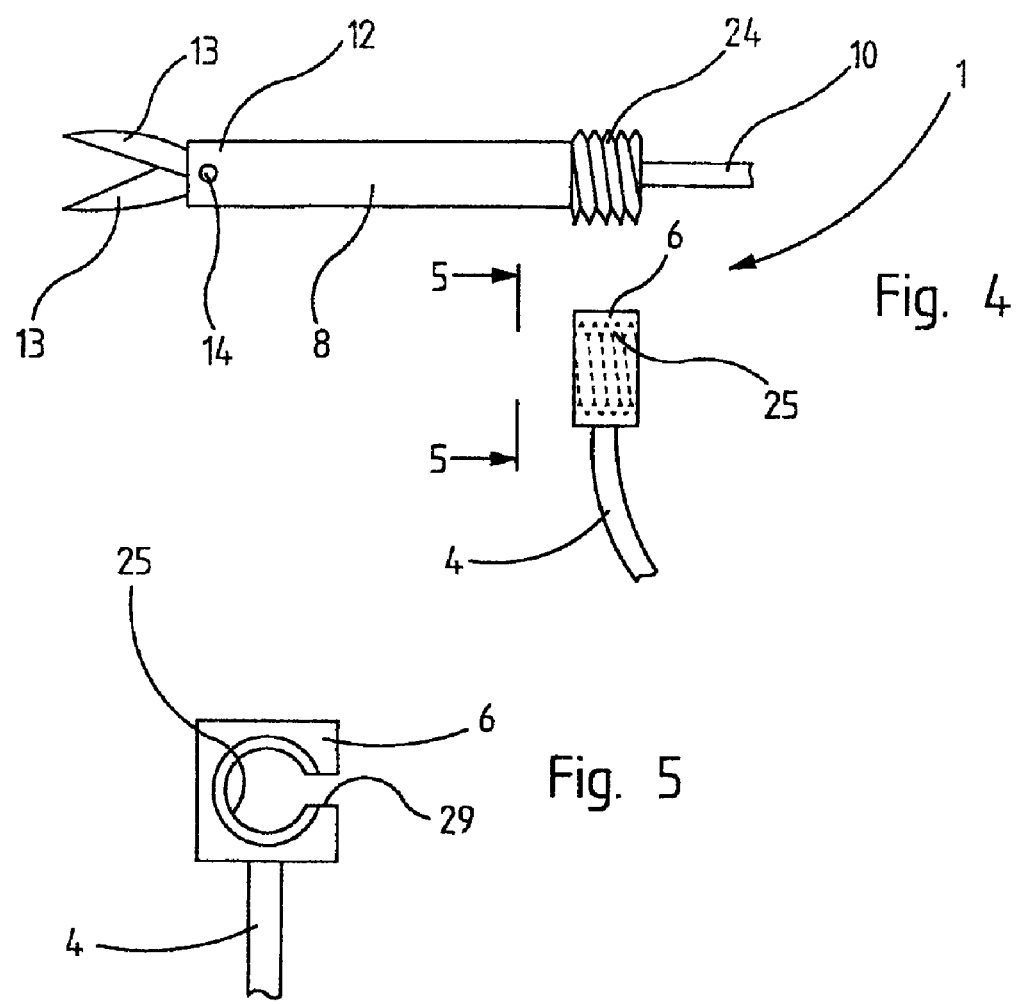
Fig. 4
Fig. 5
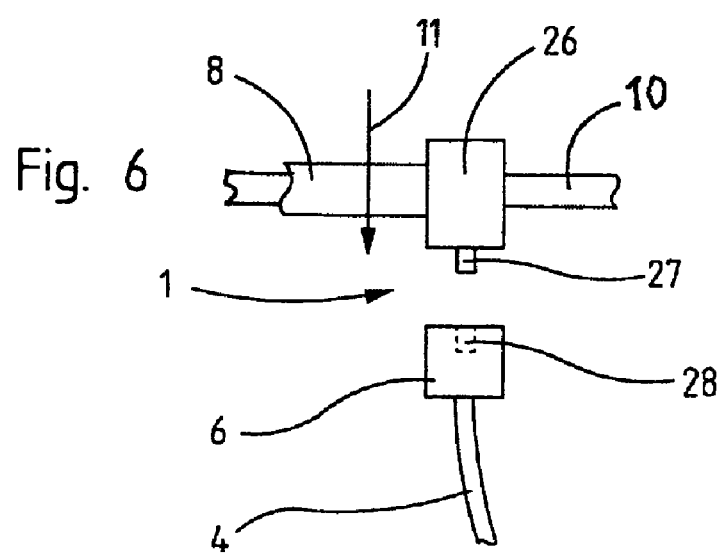
Fig. 6

JAWED SURGICAL INSTRUMENT FITTED WITH AN ELECTRODE AND A CABLE

BACKGROUND OF THE INVENTION

The present invention relates to a surgical jawed instrument.

Jawed surgical instruments of this kind are fitted with electrodes fitted at one or both of the jaw parts to apply high frequency (hf) power in single or double polar application to a tissue being cut or gripped in order to seal it by hf current. Such jawed instruments can be disassembled for cleaning.

With jawed instruments of this kind, as disclosed in the German patent document DE 94 18, 094 U, the jaw head may be locked at the distal stem end and, following unlocking, may be jointly pulled out with the actuation bar of said stem. In the process, the actuation bar is pulled distally through the tubular stem. Because the actuation bar always must be pulled through the stem tube and because a contactor is affixed to the end of the cable and cannot be pulled through the stem tube, in the relevant state of the art and also in similar jaws such as disclosed in the German patent document DE 298 23 913 U1, the cable can only be connected to the actuation bar's proximal end by a complex plug-in connection. Such a connection however is susceptible to malfunction and/or interference due to high load transmission of hf current and entails disadvantageous capacities and transition resistances adversely affecting the hf current circuit. These electrical connections in particular entail difficulties when hf generators are used that measure the tissue impedance during hf electrode loads for purposes of current control. Interfering impedances and capacitances in the connection are likely to entail spurious impedance measurements.

Jawed instruments outside the above species, such as disclosed in WO 2005/004735 A1, are more suitable, namely their cable runs uninterrupted through the full stem length and is directly connected to the electrode. However such instruments cannot be taken apart for cleaning and accordingly, are appropriate only for single use. Repeated use being precluded, the use of such instruments is very expensive.

BRIEF SUMMARY OF THE INVENTION

The object of the present invention is to create a jawed instrument of the above species offering a more advantageous cable connection.

In the present invention, the cable is firmly affixed to the actuation bar. Electrical connections no longer are present in this zone, and the otherwise interfering impedances and capacitances are also eliminated. As in the state of the art, the cable end is fitted with a connector element which cannot be pulled through the stem tube when the jaws are taken apart. The present invention solves this problem in that the actuation bar and the jaw head are connected in a manner different from that of the state of the art with the manually driven elements, namely that said actuation bar and the jaw head are detachable transversely to the stem direction or in proximal direction. This feature circumvents pulling the actuation bar and the cable through the stem tube. The unit so constituted of jaw head, actuation bar and cable may be designed for re-use by autoclaving with appropriate material selection, or if designed more simply technically, may be a single-use instrument.

The stem is required to axially transmit a force between the jaw head and the unit of manual drive elements, and may be advantageously affixed in the manner of claim 2 to the manual drive elements unit or according to claim 3 to the jaw head.

The detachable connection required by claim 2 between the jaw head and the stem or by claim 3 between the stem and the manual actuating elements may be designed according to claim 4 in a manner detachable transversely to the stem direction or according to claim 5 in a manner detachable by pulling-off in proximal direction, with matching connector parts implementing said detachable connection.

With a jawed instrument as defined in claims 2 and 4, the stem of claim 6 is fitted with a longitudinal groove which receives the actuation bar lengthwise and into within which the jaw head can be locked.

According to claim 7, in all embodiment modes, the jaw head of the present invention is rotatably supported relative to the manual actuating elements to assure conventional rotational adjustment of the jaw head.

DETAILED DESCRIPTION OF THE DRAWINGS

The appended drawings illustratively and schematically elucidate the present invention.

FIG. 1 shows a side view of a jawed instrument of the invention which can be detached transversely to the stem direction, FIG. 2 is a sectional view along line 2-2 in FIG. 1, FIG. 3 is a partial side view of FIG. 1 of an embodiment mode offering detachability in a proximal direction, FIG. 4 is a side view of FIG. 3 of an embodiment variation offering detachment in the proximal direction, FIG. 5 is a sectional view along line 5-5 of FIG. 4, and FIG. 6 is a partial side view of FIG. 4 of an embodiment variation with a stem configured at the jaw head and lateral detachability.

DETAILED DESCRIPTION OF THE INVENTION

FIGS. 1 and 2 respectively show a side view and a cross-section of a first embodiment mode of a jawed surgical instrument 1 shown taken apart, its two parts being shown one above the other. A manipulating unit 2 comprises two finger-driven levers 4 and 5 each fitted with rings receiving the actuating fingers of one hand, said levers each bearing at their upper ends drive elements 6 and 7 respectively, the distance between which is adjusted during manual actuation.

A stem 8 is affixed to the distal drive element 6. As shown in section in FIG. 2, said stem is fitted with a longitudinal groove 9 receiving an actuation bar 10 transversely to the stem direction that is in the direction of the arrow 11.

At its distal end, the actuation bar 10 is connected inside a jaw head 12 with an omitted linkage in a manner that when being longitudinally displaced relative to the jaw head 12 it will open or close two jaw parts 13 about a pin 14.

The bottom of the groove 9 is shown in dashed lines in the stem 8 of FIG. 1. The groove is indicated being slightly deeper in the distal end zone of the stem 8 for the purpose of receiving the jaw head 12. A hole 15 is configured at that site in the stem 8 and allows being engaged by a beak 16 of the jaw head 12 to affix said head in the required manner in the stem direction relative to this stem 8 and hence relative to the drive element 6.

The jaw head 12 moreover may also be locked in a manner different from that shown, in particular in a way that the jaw head shall be locked relative to the stem 8 in its stem direction while nevertheless being supported in rotatable manner.

As shown by the cross-section of FIG. 2, the actuation bar 10 is fitted by an external cross-sectional segment into the round cross-section of the stem 8 in such manner that when used laparoscopically, the stem 8 may be well sealed at its periphery.

In the zone of the drive element 7, a drive means 17 is affixed to the actuation bar 10 and in this embodiment mode is shown to be conventionally spherical. As shown in FIGS. 1 and 2, the proximal drive element 7 is fitted with a longitudinal groove 9' receiving the actuation bar 10 and further with a transverse hollow 18 receiving said drive means 17. Consequently the actuation bar 10 may be seated together with the drive means 17 in the direction of the arrow 11 into the drive element 7 while the drive means 17 is connected in pull- and push-proof manner to the drive element 7.

The jaw parts 13 of the embodiment mode of FIG. 1 are scissor blades. However they also may be jaws of forceps. One or both jaw parts 13 are fitted with omitted electrodes that shall act on the tissue to be gripped or cut. The jaw parts 13 moreover may be designed entirely as electrodes. Depending on the number of electrodes, one or two electric conductors run from the jaw head through the specifically hollowed actuation bar 10. The actuation bar 10 may act as a conductor per se.

In the present embodiment mode, an electrical two-conductor cable 20 is connected by a terminal 19 to the proximal end of the actuation bar 10 and may be hooked up by a plug 21 to an omitted hf source. The fixed connection of the cable 20 to the actuation bar 10 assures that this connection zone 19 shall be especially low in resistance and impedance and free of interference while the design of the invention is devoid of the state of the art's mandatory, detachable interconnection.

FIG. 3 shows an embodiment variation relative to FIG. 1 while retaining the same reference numerals as much as possible. The components omitted from FIG. 3 may be construed fully corresponding to those of FIG. 1.

As shown in FIG. 3, in this embodiment mode the jaw head 12 is fitted with an external thread. In this instance as in that of FIG. 1, the stem 8 is affixed to the distal drive element 6. However in the embodiment mode of FIG. 3, the stem 8 is tubular, its inside surface 22 being fitted with an inside thread 23 to mesh with the externally threaded jaw head 12. This inside thread 23 is narrower than remnant inside surface 22 of the stem 8. Accordingly the jaw head 12 is insertable from the proximal direction into the tubular stem 8 and then can be screwed into latter's distal end. Once such screw affixation has been performed, and as already cited in relation to FIG. 1, the drive means 17 can be used on the proximal drive element 7.

As regards the two embodiment modes of FIGS. 1 through 3, the stem 8 is affixed to the distal drive element 6 of the drive mechanism 2. FIG. 4 shows another embodiment mode, wherein the stem 8 is affixed to the jaw head 12. The stem 8—which is again tubular—is fitted at its proximal end with an external thread 24, whereby it may be threaded from the proximal side onto an inside thread 25 of the tubular distal drive element 6. Again, the omitted constituents of the jawed instrument 1 of FIG. 1 are present in the embodiment mode of FIG. 4.

FIG. 5 is an axial elevation relating to FIG. 4 indicating that the distal actuating part 6 may be fitted with a lateral slot 29 of a width to laterally receive the actuation bar 10. This embodiment variation—otherwise corresponding to the design of FIG. 4—also allows unscrewing the stem 8 by its external thread 24 distally out of the inside thread 25 of the distal drive element 6. Then the actuation bar 10 is laterally removed from the slot 29. This design offers the advantage that the jaw head 12 and the jaw parts 13 need not be pulled through the fully peripherally closed drive element 6 as is the case for the design described in relation to FIG. 4. Therefore, the distal end of the stem 8 at the jaw head 12 may be larger in diameter than for the embodiment shown in FIG. 4.

FIG. 6 is partial sideview of another embodiment variation while also retaining the same reference numerals. In this embodiment variation as in that of FIG. 4, the stem 8 is tubular and affixed to the jaw head 12. A connector 26 is affixed to the stem's 8 proximal end and comprises a pin 27 which may engage a hole 28 in the distal drive element 6 in the direction of the arrow 11. In this design therefore, the jaw head and the actuation bar 10 together with the stem 8 may be fitted against the manipulating unit 2 in the direction of the arrow 11 and also may be detached from it.

As illustrated in FIG. 6, the stem 8 may configured in rotatable manner in the connector 26 to allow rotating it, jointly with the jaw head 12, relative to the manipulating unit 2.

The embodiment modes of FIGS. 3-5 allow rotating the jaw head relative to the manipulating unit 2, for instance by replacing the respective screw connections 12, 23 and 24, 27 with a particular detachable clutch element, or, illustratively in the case of the embodiment mode of FIG. 3, also by a clutch between the stem 8 and the distal drive element 6. Such a rotational connection also is applicable to the embodiment mode of FIG. 1.

The embodiment mode of FIG. 1 shows that the grooves 9, 9' are open upwards. They may also be open sideways, whereby the jaw head 12, the actuation bar 10 with its drive means 17 and the proximal drive element 7 now can be inserted into the stem 8—not in the direction of the arrow 11, namely in the plane of the drawing—, but perpendicularly to it.

The invention claimed is:

1. A jawed surgical instrument fitted at a distal end with a jaw head which is affixed to a longitudinally elongated stem and which supports two mutually oppositely displaceable jaw parts, said jaw head being connectable by means of an actuation bar to one of two drive elements of a manipulating unit that are mutually oppositely displaceable in a stem direction, the other of said drive elements being connected to the stem, said jaw head comprising at least one electrode designed for tissue engagement and being electrically connected by means of the actuation bar to an electric cable issuing from said bar, the actuation bar and the jaw head being detachably connected to the manipulating unit, wherein the actuation bar and the jaw head are removable in a direction transverse to the stem direction or in a direction proximal and parallel to the stem, and wherein the electric cable is non-detachably affixed to the actuation bar.

2. The jawed instrument as claimed in claim 1, wherein the stem is affixed to the manipulating unit and is connected to the jaw head.

3. The jawed instrument as claimed in claim 2, wherein the detachable connection is detachable in the transverse direction relative to the stem direction.

4. The jawed instrument as claimed in claim 3, wherein the stem is fitted with a longitudinal groove receiving the actuation bar and in that the jaw head may be locked in place in said groove.

5. The jawed instrument as claimed in claim 2, wherein the detachable connection is detachable in the proximal direction parallel to the stem direction.

6. The jawed instrument as claimed in claim 2, wherein the stem is fitted with a longitudinal groove receiving the actuation bar and wherein the jaw head may be locked in place in said groove.

7. The jawed instrument as claimed in claim 1, wherein the stem is affixed to the jaw head and is detachably connected to the manipulating unit.

8. The jawed instrument as claimed in claim 7, wherein the detachable connection is detachable in the transverse direction relative to the stem direction.

9. The jawed instrument as claimed in claim 7, wherein the detachable connection is detachable in the proximal direction parallel to the stem direction.

10. The jawed instrument as claimed in claim 1, wherein the jaw head is rotatable relative to the manipulation unit around the stem direction.

\* \* \* \* \*